United States Patent
Pierce et al.

(10) Patent No.: US 11,246,312 B2
(45) Date of Patent: Feb. 15, 2022

(54) ANTIMICROBIAL COMPOSITIONS AND METHODS OF USING SAME

(71) Applicant: CROWPIERCE TECHNOLOGIES, LLC, Canton, GA (US)

(72) Inventors: George Pierce, Canton, GA (US); Sidney Crow, Canton, GA (US); Amber Keller, Canton, GA (US)

(73) Assignee: CROWPIERCE TECHNOLOGIES, LLC, Canton, GA (US)

(*) Notice: Subject to any disclaimer, the term of this patent is extended or adjusted under 35 U.S.C. 154(b) by 124 days.

(21) Appl. No.: 16/475,878

(22) PCT Filed: Jan. 5, 2018

(86) PCT No.: PCT/US2018/012457
§ 371 (c)(1),
(2) Date: Jul. 3, 2019

(87) PCT Pub. No.: WO2018/129233
PCT Pub. Date: Jul. 12, 2018

(65) Prior Publication Data
US 2019/0343894 A1 Nov. 14, 2019

Related U.S. Application Data

(60) Provisional application No. 62/442,656, filed on Jan. 5, 2017.

(51) Int. Cl.
| | |
|---|---|
| *A01N 65/22* | (2009.01) |
| *A23L 33/105* | (2016.01) |
| *A23L 33/115* | (2016.01) |
| *A23L 33/135* | (2016.01) |
| *A01N 47/44* | (2006.01) |
| *A23C 9/12* | (2006.01) |
| *A23C 9/152* | (2006.01) |
| *A61K 31/785* | (2006.01) |
| *A61K 35/74* | (2015.01) |
| *A61K 36/534* | (2006.01) |
| *A01N 63/10* | (2020.01) |

(52) U.S. Cl.
CPC ............ *A01N 65/22* (2013.01); *A01N 47/44* (2013.01); *A01N 63/10* (2020.01); *A23C 9/1203* (2013.01); *A23C 9/152* (2013.01); *A23L 33/105* (2016.08); *A23L 33/115* (2016.08); *A23L 33/135* (2016.08); *A61K 31/785* (2013.01); *A61K 35/74* (2013.01); *A61K 36/534* (2013.01)

(58) Field of Classification Search
CPC .................................................... A01N 65/22
See application file for complete search history.

(56) References Cited

U.S. PATENT DOCUMENTS

| | | |
|---|---|---|
| 5,403,587 A | 4/1995 | Mccue et al. |
| 6,346,281 B1 | 2/2002 | Death et al. |
| 6,846,498 B2 | 1/2005 | Death et al. |
| 7,763,575 B2 | 7/2010 | Weiss et al. |
| 8,343,945 B2 | 1/2013 | Tamarkin et al. |
| 2005/0214386 A1 | 9/2005 | Shaheen et al. |
| 2007/0092545 A1 | 4/2007 | Bale et al. |
| 2008/0311231 A1 | 12/2008 | Modak et al. |
| 2010/0215775 A1 | 8/2010 | Schmaus et al. |
| 2012/0201902 A1 | 8/2012 | Modak et al. |
| 2012/0237556 A1 | 9/2012 | Schlessinger et al. |
| 2013/0230609 A1 | 9/2013 | Modak et al. |
| 2016/0015031 A1 | 1/2016 | Pesaro et al. |

FOREIGN PATENT DOCUMENTS

| | | |
|---|---|---|
| KR | 101260371 B1 | 5/2013 |
| WO | 02068335 A2 | 9/2002 |

OTHER PUBLICATIONS

Zaidi et al., "In vitro antimicrobial activity, phytochemical analysis and total phenolic content of essential oil from Mentha spicata and Mentha piperata," Int. Food Res. J. 22(6):2440-2445, 2015.*
International Search Report and Written Opinion dated Mar. 20, 2018 in International Application PCT/US18/12457 (8 pages).
International Preliminary Report on Patentability dated Jul. 18, 2019 in International Application PCT/US18/12457 (6 pages).
PCT/US2018/012457; International Search Report and Written Opinion dated Mar. 20, 2018 (7 pages).

* cited by examiner

*Primary Examiner* — Rosanne Kosson
(74) *Attorney, Agent, or Firm* — Meunier Carlin & Curfman LLC

(57) ABSTRACT

Disclosed herein are antimicrobial compositions that are substantially odorless. The antimicrobial compositions can comprise, for example, a first essential oil and a second essential oil, wherein the composition is substantially odorless. In some examples, the composition can further comprise a third essential oil. The compositions described herein can, for example, reduce the population of microbes, such as *Staphylococcus aureus* or *Escherichia coli*, by 5 log or more. Also disclosed herein are beverages and food products including the compositions disclosed herein. Also disclosed herein is milk including the compositions disclosed herein. Also disclosed herein are methods for treating or preventing a microbial infection in a subject, the methods comprising administering to the subject an effective amount of any of the compositions disclosed herein. Also disclosed herein are methods for combating bovine mastitis, the methods comprising applying any of the compositions disclosed herein to cow udders.

16 Claims, No Drawings

ANTIMICROBIAL COMPOSITIONS AND METHODS OF USING SAME

CROSS-REFERENCE TO RELATED APPLICATIONS

This application claims the benefit of priority to U.S. Provisional Application No. 62/442,656, filed Jan. 5, 2017, which is hereby incorporated herein by reference in its entirety.

BACKGROUND

Essential oils have been used for centuries in perfumes, colognes, splashes, soaps, creams, etc. While the application of essential oils in essences, fragrances perfumes, colognes, etc. is well established, the use of essential oils in applications where no detectable odor is preferred or required is limited.

SUMMARY

Disclosed herein are antimicrobial compositions that are substantially odorless. The antimicrobial compositions can comprise, for example, a first essential oil and a second essential oil, wherein the composition is substantially odorless. In some examples, the composition can further comprise a third essential oil. Substantially odorless, as used herein, means the composition is substantially not detected by olfaction. In some examples, the compositions can have a pH of 7.5 or less.

In some examples, the first essential oil, second essential oil, and/or third essential oil can be selected from spearmint oil, thyme oil, sandalwood oil, and combinations thereof. In some examples, the first essential oil is spearmint oil and the second essential oil is thyme oil. In some examples, the first essential oil is spearmint oil, the second essential oil is thyme oil, and the third essential oil is sandalwood oil. The first essential oil, the second essential oil, and/or the third essential oil can each be present in a concentration of from 0.05% to 0.2% by weight.

As used herein, antimicrobials include, for example, antibacterials, antifungals, and antivirals. In some examples, the microbes are one or more microorganisms selected from the group consisting of *Staphylococcus aureus* and *Escherichia coli*. In some examples, the compositions described herein can result in a reduction in the population of microbes of 5 log or more.

In some examples, the compositions can further comprise polyhexamethylene biguanide (PHMB). In some examples, the polyhexamethylene biguanide can be present in an amount of from 100 ppm to 2000 ppm.

Also disclosed herein are beverages and food products including the compositions disclosed herein. Also disclosed herein is milk including the compositions disclosed herein.

Also disclosed herein are methods for treating or preventing a microbial infection in a subject, the methods comprising administering to the subject an effective amount of any of the compositions disclosed herein. Also disclosed herein are methods for combating bovine mastitis, the methods comprising applying any of the compositions disclosed herein to cow udders.

DETAILED DESCRIPTION

Disclosed herein are antimicrobial compositions that are substantially odorless. The antimicrobial compositions can comprise, for example, a first essential oil and a second essential oil, wherein the composition is substantially odorless. In some examples, the composition can further comprise a third essential oil.

It is understood that throughout this specification the identifiers "first," "second," and "third" are used solely to aid in distinguishing the various components and steps of the disclosed subject matter. The identifiers "first," "second," and "third" are not intended to imply any particular order, amount, preference, or importance to the components or steps modified by these terms.

Substantially odorless, as used herein, means the composition is substantially not detected by olfaction, i.e., an olfactometer test, as described herein. An odor emission often consists of a complex mixture of many odorous compounds. Analytical monitoring of individual chemical compounds present in such odor is usually not practical. As a result, odor sensory methods, instead of instrumental methods, are normally used to measure odor.

The sense of smell gives rise to the perception of odors, mediated by the olfactory nerve. In humans, the olfactory receptor cells are neurons present in the olfactory epithelium, a small patch of tissue in back of the nasal cavity. There are millions of olfactory receptor neurons that act as sensory signaling cells. Each neuron has cilia in direct contact with air. Odorous molecules act as a chemical stimulus by binding to receptor proteins extending form the cilia and thereby initiating an electric signal. When the signal reaches a threshold, the neuron fires, sending a signal traveling along the axon to the olfactory bulb, part of the limbic system of the brain, where interpretation of the smell begins.

Odor sensation usually depends on the concentration available to the olfactory receptors. A single odorant stimulus type is typically recognized by multiple receptors, and different odorants are recognized by combinations of receptors, the patterns of neuron signals helping identify the smell. The olfactory system does not interpret a single compound, but instead the whole odorous mix, not necessarily corresponding to concentration or intensity of any single constituent.

Sensation of odor has four properties related to threshold and tolerance: odor concentration, odor intensity, odor quality, and hedonic tone. Odor concentration is an odor's pervasiveness. To measure odor sensation, an odor is diluted to certain amounts to reach a detection or recognition threshold. The detection threshold is the concentration of an odor in air when 50% of a population can distinguish between the odorous sample and an odor free reference sample.

The measurement of odor concentration is the most widespread method to quantify odors. To establish the odor concentration, an olfactometer test is used. "Substantially odorless," as used herein, means that the composition is substantially not detected by an olfactometer test. An olfactometer test can employ a panel (e.g., a plurality) of human noses as sensors. In the olfactometry testing procedure, a test composition and an odor-free gas (e.g., a reference) are presented separately from sniffing ports to the panelists, who are housed in an odor-neutral room. The panelists are asked to compare the gases emitted from each sniffing port, after which each of the panelists are asked to report the presence (or absence) of odor together with a confidence level (e.g., guessing, inkling, certainty, etc.) of their assessment. The concentration of the test composition is then changed (e.g., increased or decreased) and the panelists are asked to repeat their assessment. This continues over a range of concentrations for the test composition. The responses of the panelists over a range of concentrations can then be used to calculate the concentration of the odor in terms of European Odor Units (ouE/m$^3$).

Odor intensity is the perceived strength of odor sensation, which is measured in conjunction with odor concentration and can be modeled by the Weber-Fechner law:

$$I = a \log(c) + b$$

where I is the perceived psychological intensity at the dilution step on the butanol scale, a is the Weber-Fechner coefficient, c is the chemical concentration, and b is the intercept constant. Odor intensity can also be expressed using an odor intensity scale, which is a verbal description of an odor sensation to which a numerical value is assigned. Odor intensity can be divided into the following categories according to intensity: 0—no odor; 1—very weak (odor threshold); 2—weak; 3—distinct; 4—strong; 5—very strong; and 6—intolerable. This method can be applied in the laboratory by a series of suitably trained panelists.

Odor quality, or the character of an odor, is the ability to distinguish different odors, and is only descriptive. Most commonly, a set of standard descriptors is used.

Hedonic tone assessment is the process of scaling odors on a scale ranging from extremely unpleasant to neutral to extremely pleasant. Intensity and hedonic tone, while similar, refer to different things, namely the strength of the odor (intensity) and the pleasantness of the odor (hedonic tone). Moreover, it is important to note that perception of an odor may change from pleasant to unpleasant with increasing concentration, intensity, time, frequency, and previous experience with a specific odor, all factors determining a response. The overall set of qualities are sometimes identified as the FIDOL factors, which is short for Frequency, Intensity, Duration, Offensiveness, and Location.

An essential oil, as used herein, refers to a volatile oil derived from a natural source, such as a plant (e.g., from the leaves, stem, slower, twigs, or skin). An essential oil usually carries the characteristic odor or flavor (e.g., the essence) of the source from which it was derived. Some essential oils can comprise a single compound, whereas others can comprise a plurality of compounds. Essential oils can be hydrophobic, lipophilic, or a combination thereof.

Essential oils can be derived from their sources by a variety of methods, which include, but are not limited to, distillation (e.g., steam distillation), expression (e.g., pressing, such as cold-pressing), solvent extraction, maceration, enfleurage, and combinations thereof. Examples of sources of essential oils include, but are not limited to, agarwood, allspice, almond, anise, basil, bay leaf, benzoin, bergamot, cannabis, camphor, cassia, cedar, celery, chamomile, cinnamon, copaiba, clary sage, clove, cumin, *eucalyptus*, frankincense, galangal, geranium, ginger, grapefruit, guava, hops, hyssop, jasmine, juniper, lavender, lemon, lemongrass, lime, manuka, marjoram, melaleuca, myrrh, nutmeg, orange, oregano, patchouli, peppermint, pine, rose, rosemary, rosewood, sage, sandalwood, sassafras, spearmint, tangerine, tea tree, thyme, tsuga, valerian, and wintergreen.

Examples of essential oils include, but are not limited to, agar oil (*Aquilaria malaccensis* oil), ajwain oil (*Carum copticum* oil), *angelica* root oil (*Angelica archangelica* oil), anise oil (*Pimpinella anisom* oil), asafetida oil, Balsam of Peru oil, basil oil, bay oil, bergamot oil, black pepper oil (*Piper nigrum* oil), birch oil, camphor, cannabis oil, caraway oil, cardamom oil, carrot oil, cedarwood oil, chamomile oil, calamus root oil, cinnamon oil, *Cistus* oil, citron oil, citronella oil, clary sage oil, clove oil, coffee oil, coriander oil, costmary oil (*Tanacetum blasamita* oil), costus root oil, cranberry seed oil, cubeb oil, cumin oil, cypress oil, cypriol oil, curry leaf oil, davana oil (*Atemisia pollens* oil), dill oil, elecampane oil, *eucalyptus* oil (*Eucalyptus globulus* oil), fennel seed oil, fenugreek oil, fir oil, frankincense oil, galangal oil, galbanum oil, garlic oil, geranium oil, ginger oil, goldenrod oil, grapefruit oil, henna oil, helichrysum oil, hickory nut oil, horseradish oil, hyssop oil, Idaho Tansy oil, ironwort oil, jasmine oil, juniper berry oil, *Larus nobilis* oil, lavender oil, *ledum* oil, leleshwa oil, lemon oil, lemon myrtle oil, lemongrass oil, lime oil, *Litsea cubeba* oil, linaloe oil, mandarin oil, marjoram oil, Melissa oil (Lemon balm oil), *Metha arvensis* oil (mint oil), Mountain Savoy oil, mustard seed oil, myrrh oil, neem oil, neroli oil, *Nigella sativa* oil, nutmeg oil, onion oil, orange oil, oregano oil, orris oil, palo santo oil, parsley oil, patchouli oil, perilla oil, peppermint oil, petitgrain oil, pine oil, ravensara oil, red cedar oil, roman chamomile oil, rose oil, rosehip oil (*Rosa rubiginosa* or *Rosa mosqueta* oil), rosemary oil (*Rosmarinus officinalis* oil), rosewood oil, sage oil, sandalwood oil, sassafras oil, savory oil (*satureja* oil), *schisandra* oil (*Schisandra chinensis* oil), spearmint oil, spikenard oil, spruce oil, star anise oil, tangerine oil, tarragon oil (*Artemisia dracunculus* oil), tea tree oil (*Melaluca alternifolia* oil), thyme oil, tsuga oil, turmeric oil, valerian oil, vetiver oil, western red cedar oil, wintergreen oil, yarrow oil, ylang-ylang oil, and zedoary oil.

In some examples, the first essential oil, second essential oil, and/or third essential oil can be selected from spearmint oil, thyme oil, sandalwood oil, and combinations thereof. In some examples, the first essential oil is spearmint oil and the second essential oil is thyme oil. In some examples, the first essential oil is spearmint oil, the second essential oil is thyme oil, and the third essential oil is sandalwood oil. In some embodiments, the composition can include more than three essential oils. In some embodiments, one or more, two or more, or all of the essential oils used in the composition possess an odor when used alone, but produce an odorless composition when used together in the amounts provided herein.

The first essential oil, the second essential oil, and/or the third essential oil can be present in a concentration of 0.05% by weight or more (e.g., 0.06% by weight or more, 0.07% by weight or more, 0.08% by weight or more, 0.09% by weight or more, 0.10% by weight or more, 0.11% by weight or more, 0.12% by weight or more, 0.13% by weight or more, 0.14% by weight or more, 0.15% by weight or more, 0.16% by weight or more, 0.17% by weight or more, 0.18% by weight or more, or 0.19% by weight or more). The first essential oil, the second essential oil, and/or the third essential oil can be present in a concentration of 0.2% by weight or less (e.g., 0.19% by weight or less, 0.18% by weight or less, 0.17% by weight or less, 0.16% by weight or less, 0.15% by weight or less, 0.14% by weight or less, 0.13% by weight or less, 0.12% by weight or less, 0.11% by weight or less, 0.10% by weight or less, 0.09% by weight or less, 0.08% by weight or less, 0.07% by weight or less, or 0.06% by weight or less).

The concentration of the first essential oil, the second essential oil, and/or the third essential oil can range from any of the minimum values described above to any of the maximum values described above. For example, the first essential oil, the second essential oil, and/or the third essential oil can be present in a concentration of from 0.05% to 0.2% by weight (e.g., from 0.05% to 0.12% by weight, from 0.12% to 0.2% by weight, from 0.05% to 0.08% by weight, from 0.08% to 0.12% by weight, from 0.12% to 0.16% by weight, from 0.16% to 0.2% by weight, from 0.07% to 0.18% by weight, or from 0.09 to 0.16% by weight).

As used herein, "antimicrobial" refers to the ability to treat or control (e.g., reduce, prevent, treat, or eliminate) the growth of a microbe at any concentration. Similarly, the terms "antibacterial," "antifungal," and "antiviral" refer to the ability to treat or control the growth of bacteria, fungi, and viruses at any concentration, respectively.

As used herein, "reduce" or other forms of the word, such as "reducing" or "reduction," refers to lowering of an event or characteristic (e.g., microbe population/infection). It is understood that the reduction is typically in relation to some standard or expected value. For example, "reducing microbial infection" means reducing the spread of a microbial infection relative to a standard or a control.

As used herein, "prevent" or other forms of the word, such as "preventing" or "prevention," refers to stopping a particular event or characteristic, stabilizing or delaying the development or progression of a particular event or characteristic, or minimizing the chances that a particular event or characteristic will occur. "Prevent" does not require comparison to a control as it is typically more absolute than, for example, "reduce." As used herein, something could be reduced but not prevented, but something that is reduced could also be prevented. Likewise, something could be prevented but not reduced, but something that is prevented could also be reduced.

As used herein, "treat" or other forms of the word, such as "treated" or "treatment," refers to administration of a composition or performing a method in order to reduce, prevent, inhibit, or eliminate a particular characteristic or event (e.g., microbe growth or survival). The term "control" is used synonymously with the term "treat."

As used herein, antimicrobials include, for example, antibacterials, antifungals, and antivirals. Examples of microbes include, but are not limited to adenoviruses, astrovirus, bacillus bacteria, *Blastomyces dermatitidis*, Bovine coronavirus, bovine viral diarrhea, *Brucella melitensis*, clostridium bacteria, *Coccidioides immitis*, common cold (e.g., rhinoviruses such as rhinovirus A, rhinovirus B, and rhinovirus C), *Corynebacterium bovis, Cryptococcus neoformans*, echovirus, enteroviruses, *Enterobacter aerogenes, Escherichia coli, Feline calicivirus* (FCV), flu virus (e.g., hepatitis A, hepatitis B, herpes simplex viruses (e.g., herpes simplex1, herpes simplex 2), *Histoplasma capsulatum*, Human Immunodeficiency Virus (HIV), influenza viruses such as influenza A, influenza virus B, and influenza virus C), *Klebsiella pneumoniae, Klebsiella oxytoca, Mycobacterium tuberculosis, Mycoplasma* spp., norovirus, *Pasteurella* spp., poliovirus (e.g., polio virus type 1), *Proteus* spp., *Pseudomonas aeruginosa, Respiratory syncytial* virus (RSV), rotavirus, *Salmonella typhosa, Serratia marcescens, Staphylococcus aureus, Staphylococcus epidermidis, Streptococcus agalactiae, Streptococcus pyogenes, Streptococcus uberis, Trueperella pyogenes*, and *vaccinia* virus. In some examples, the microbes are one or more microorganisms selected from the group consisting of *Staphylococcus aureus* and *Escherichia coli*.

The activity of the compositions provided herein as antimicrobial agents can be measured in standard assays, e.g., HPLC assays. The compositions can be evaluated for antibacterial activity using the Mueller Hinton (MH) broth antibacterial assay as specified by the Clinical and Laboratory Standards Institute MIC broth microdilution protocol (see Methods for Dilution Antimicrobial Susceptibility Tests for Bacteria That Grow Aerobically; Approved Standard, In *The Clinical and Laboratory Standards Institute (CLSI, formerly NCCLS)*, $7^{th}$ ed., January 2006, 26 (2), M7-A7; see also Performance Standards for Antimicrobial Susceptibility Testing; Eighteenth Informational Supplement, In *The Clinical and Laboratory Standards Institute (CLSI, formerly NCCLS)*, January 2008, 28 (1), M100-S18.

In some examples, the compositions described herein can result in a reduction in the population of microbes of 5 log or more (e.g., 5.5 log or more, 6 log or more, 6.5 log or more, or 7 log or more). In some examples, the compositions described herein can result in a reduction in the population of microbes of 5 log or more in 30 seconds (e.g., population of microbes exposed to the composition for 30 seconds). In some examples, the compositions described herein can result in complete (100%) reduction in the population of microbes.

In some examples, the compositions can have a pH of 7.5 or less (e.g., pH 7 or less, pH 6.5 or less, pH 6 or less, pH 5.5 or less, pH 5 or less, pH 4.5 or less, pH 4 or less, pH 3.5 or less, pH 3 or less, or pH 2.5 or less). In some examples, the compositions can have a pH of 2 or more (e.g., pH 2.5 or more, pH 3 or more, pH 3.5 or more, pH 4 or more, pH 4.5 or more, pH 5 or more, pH 5.5 or more, pH 6 or more, pH 6.5 or more, or pH 7 or more). The pH of the compositions can range from any of the minimum values described above to any of the maximum values described above. For example, the compositions can have a pH of from 2 to below 7.5 (e.g., pH from 2 to 4.5, pH from 4.5 to 7.5, pH from 2 to 3, pH from 3 to 4, pH from 4 to 5, pH from 5 to 6, pH from 6 to 7.5, or pH from 3 to 6).

Depending on the intended mode of administration, the compositions can be in the form of solid, semi-solid or liquid dosage forms, such as, for example, powders, liquids, or suspensions. The form of the composition can, for example, depend on the intended mode of administration or method of use. The compositions described herein can, for example, be in the form of a soap, a cleanser, a shampoo, a dip, a splash, a lotion, a cosmetic, a toothpaste, or a laundry product.

In some examples, the compositions can further comprise a carrier, such as a pharmaceutically acceptable carrier. As used herein, "pharmaceutically acceptable" refers to a material that is not biologically or otherwise undesirable, which can be administered to an individual along with the selected compositions without causing unacceptable biological effects or interacting in a deleterious manner with the other components of the compositions in which it is contained. In some examples, the compositions further comprising pharmaceutically acceptable carrier are referred to as pharmaceutically acceptable formulations. A pharmaceutically acceptable formulation refers to those formulations of the compositions described herein that are within the scope of sound medical judgment, suitable for use in contact with the tissues of subjects without undue toxicity, irritation, allergic response, and the like, commensurate with a reasonable benefit/risk ratio, and effective for their intended use.

As used herein, the term carrier encompasses any excipient, diluent, filler, salt, buffer, stabilizer, solubilizer, lipid, surfactant, solvent, thickener, wax, or other material well known in the art for use in such formulations. The choice of a carrier for use in a composition will depend upon the intended route of administration for the composition. The preparation of pharmaceutically acceptable carriers and formulations containing these materials is described in, e.g., *Remington's Pharmaceutical Sciences*, 21st Edition, ed. University of the Sciences in Philadelphia, Lippincott, Williams & Wilkins, Philadelphia Pa., 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.).

Liquid forms of the compositions described herein or derivatives thereof can include pharmaceutically acceptable emulsions, solutions, suspensions, syrups, and elixirs. In addition to the active compositions, the liquid forms can contain inert diluents commonly used in the art, such as water or other solvents, solubilizing agents, and emulsifiers, such as for example, acetone, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, or suspending agents. Suspensions, in addition to the active composition, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

The compositions described herein for topical administrations can be prepared, for example, by mixing the composition with suitable non-irritating excipients, emollients, or carriers such as cocoa butter, polyethyleneglycol or a wax.

Ophthalmic formulations, ointments, powders, and solutions (e.g., eye drops) are also contemplated as being within the scope of the compositions.

In some examples, the composition can additionally comprise a surfactant. In some examples, the surfactant is selected from the group consisting of cocoamine oxide (e.g., Barlox 12), alkyl polyglucosides (e.g., Glucopon 225 DK), sodium alkyl sulfonates (e.g., Witconate), and combinations thereof. In some embodiments, the composition can additionally comprise a thickener such as hydroxyethylcellulose (e.g., Natrosol).

In some examples, the compositions disclosed herein can further comprise an additional antimicrobial agent, such as an additional antibacterial agent, an additional antiviral agent, and/or an additional antifungal agent. The additional antimicrobial agent can include any antimicrobial agent consistent with the compositions and methods described herein.

Examples of additional antimicrobial agents include, for example, alexidine, asphodelin A, atromentin, auranthine, austrocortilutein, austrocortirubin, azerizin, chlorbisan, chloroxine, cidex, cinoxacin, citreorosein, copper usnate, cupiennin, curvularin, DBNPA, dehydrocurvularin, desoxy-fructo-serotonin, dichloroisocyanuric acid, elaiomycin, holtfreter's solution, malettinin, naphthomycin, neutrolin, niphimycin, nitrocefin, oxadiazoles, paenibacterin, proclin, ritiometan, ritipenem, silicone quaternary amine, stylisin, taurolidine, tirandamycin, trichloroisocyanuric acid, and triclocarban.

Examples of antibacterials include, for example, acetoxycycloheximide, aciduliprofundum, actaplanin, actinorhodin, alazopeptin, albomycin, allicin, allistatin, allyl isothiocyanate, ambazone, aminocoumarin, aminoglycosides, 4-aminosalicylic acid, ampicillin, ansamycin, anthramycin, antimycin A, aphidicolin, aplasmomycin, archaeocin, arenicin, arsphenamine, arylomycin A2, ascofuranone, aspergillic acid, avenanthramide, avibactam, azelaic acid, bafilomycin, bambermycin, beauvericin, benzoyl peroxide, blasticidin S, bottromycin, brilacidin, caprazamycin, carbomycin, cathelicidin, cephalosporins, ceragenin, chartreusin, chromomycin A3, citromycin, clindamycin, clofazimine, clofoctol, clorobiocin, coprinol, coumermycin A1, cyclic lipopeptides, cycloheximide, cycloserine, dalfopristin, dapsone, daptomycin, debromomarinone, 17-dimethylaminoethylamino-17-demethoxygeldanamycin, echinomycin, endiandric acid C, enediyne, enviomycin, eravacycline, erythromycin, esperamicin, etamycin, ethambutol, ethionamide, (6S)-6-fluoro-shikimic acid, fosfomycin, fosmidomycin, friulimicin, furazolidone, furonazide, fusidic acid, geldanamycin, gentamycin, gepotidacin, glycyciclines, glycyrrhizol, gramicidin S, guanacastepene A, hachimycin, halocyamine, hedamycin, helquinoline, herbimycin, hexamethylenetetramine, hitachimycin, hydramacin-1, isoniazid, kanamycin, katanosin, kedarcidin, kendomycin, kettapeptin, kidamycin, lactivicin, lactocillin, landomycin, landomycinone, lasalocid, lenapenem, leptomycin, lincosamides, linopristin, lipiarmycins, macbecin, macrolides, macromomycin B, maduropeptin, mannopeptimycin glycopeptide, marinone, meclocycline, melafix, methylenomycin A, methylenomycin B, monensin, moromycin, mupirocin, mycosubtilin, myriocin, myxopyronin, naphthomycin A, narasin, neocarzinostatin, neopluramycin, neosalvarsan, neothramycin, netropsin, nifuroxazide, nifurquinazol, nigericin, nitrofural, nitrofurantoin, nocathiacin I, novobiocin, omadacycline, oxacephem, oxazolidinones, penicillins, peptaibol, phytoalexin, plantazolicin, platensimycin, plectasin, pluramycin A, polymixins, polyoxins, pristinamycin, pristinamycin IA, promin, prothionamide, pulvinone, puromycin, pyocyanase, pyocyanin, pyrenocine, questiomycin A, quinolones, quinupristin, ramoplanin, raphanin, resistome, reuterin, rifalazil, rifamycins, ristocetin, roseophilin, salinomycin, salinosporamide A, saptomycin, saquayamycin, seraticin, sideromycin, sodium sulfacetamide, solasulfone, solithromycin, sparassol, spectinomycin, staurosporine, streptazolin, streptogramin, streptogramin B, streptolydigin, streptonigrin, styelin A, sulfonamides, surfactin, surotomycin, tachyplesin, taksta, tanespimycin, telavancin, tetracyclines, thioacetazone, thiocarlide, thiolutin, thiostrepton, tobramycin, trichostatin A, triclosan, trimethoprim, trimethoprim, tunicamycin, tyrocidine, urauchimycin, validamycin, viridicatumtoxin B, vulgamycin, xanthomycin A, and xibornol.

Examples of antifungals include, for example, abafungin, acibenzolar, acibenzolar-S-methyl, acrisorcin, allicin, aminocandin, amorolfine, amphotericin B, anidulafungin, azoxystrobin, bacillomycin, *Bacillus pumilus*, barium borate, benomyl, binapacryl, boric acid, bromine monochloride, bromochlorosalicylanilide, bupirimate, butenafine, candicidin, caprylic acid, captafol, captan, carbendazim, caspofungin, cerulenin, chloranil, chlormidazole, chlorphetanol, chlorothalonil, chloroxylenol, chromated copper arsenate, ciclopirox, cilofungin, cinnamaldehyde, clioquinol, copper (I) cyanide, copper(II) arsenate, cruentaren, cycloheximide, davicil, dehydroacetic acid, dicarboximide fungicides, dichlofluanid, dimazole, diphenylamine, echinocandin, echinocandin B, epoxiconazole, ethonam, falcarindiol, falcarinol, famoxadone, fenamidone, fenarimol, fenpropimorph, fentin acetate, fenticlor, filipin, fluazinam, fluopicolide, flusilazole, fluxapyroxad, fuberidazole, griseofulvin, halicylindramide, haloprogin, hamycin, hexachlorobenzene, hexachlorocyclohexa-2,5-dien-1-one, 5-hydroxy-2(5H)-furanone, iprodione, lime sulfur, mancozeb, maneb, melafix, metalaxyl, metam sodium, methylisothiazolone, methylparaben, micafungin, miltefosine, monosodium methyl arsenate, mycobacillin, myclobutanil, natamycin, beta-nitrostyrene, nystatin, paclobutrazol, papulacandin B, parietin, pecilocin, pencycuron, pentamidine, pentachloronitrobenzene, pentachlorophenol, perimycin, 2-phenylphenol, polyene antimycotic, propamocarb, propiconazole, pterulone, ptilomycalin A, pyrazophos, pyrimethanil, pyrrolnitrin, selenium disulfide, sparassol, strobilurin, sulbentine, tavaborole, tebuconazole, terbinafine, theonellamide F, thymol, tiabendazole, ticlatone, tolciclate, tolnaftate, triadimefon, triamiphos, tribromometacresol, 2,4,6-tribromophenol, tributyltin oxide, triclocarban, triclosan, tridemorph, trimetrexate, undecylenic acid, validamycin, venturicidin, vinclozolin, vinyldithiin, vusion, xanthene, zinc borate, zinc pyrithione, zineb and ziram.

Examples of antivirals include, but are not limited to, afovirsen, alisporivir, angustific acid, angustifodilactone, alovudine, beclabuvir, 2,3-bis(acetylmercaptomethyl)quinoxaline, brincidofovir, dasabuvir, docosanol, fialuridine, ibacitabine, imiquimod, inosine, inosine pranobex, interferon, metisazone, miltefosine, neokadsuranin, neotripterifordin, ombitasvir, oragen, oseltamivir, pegylated interferon, podophyllotoxin, radalbuvir, semapimod, tecovirimat, telbivudine, theaflavin, tilorone, triptofordin C-2, variecolol and ZMapp.

In some examples, the compositions can further comprise polyhexamethylene biguanide (PHMB). In some examples, the polyhexamethylene biguanide can be present in an amount of 100 ppm or more (e.g., 200 ppm or more, 300 ppm or more, 400 ppm or more, 500 ppm or more, 600 ppm or more, 700 ppm or more, 800 ppm or more, 900 ppm or more, 1000 ppm or more, 1100 ppm or more, 1200 ppm or more, 1300 ppm or more, 1400 ppm or more, 1500 ppm or more, 1600 ppm or more, 1700 ppm or more, 1800 ppm or more, or 1900 ppm or more). In some examples, the polyhexamethylene biguanide can be present in an amount of 2000 ppm or less (e.g., 1900 ppm or less, 1800 ppm or less, 1700 ppm or less, 1600 ppm or less, 1500 ppm or less, 1400 ppm or less, 1300 ppm or less, 1200 ppm or less, 1100 ppm or less, 1000 ppm or less, 900 ppm or less, 800 ppm or less, 700 ppm or less, 600 ppm or less, 500 ppm or less, 400 ppm or less, 300 ppm or less, or 200 ppm or less). The amount of polyhexamethylene biguanide present in the composition can range from any of the minimum values described above to any of the maximum values described above. For example, the polyhexamethylene biguanide can be present in an amount of from 100 ppm to 2000 ppm (e.g., from 100 ppm to 1000 ppm, from 1000 ppm to 2000 ppm, from 100 ppm to 500 ppm, from 500 ppm to 1000 ppm, from 1000 ppm to 1500 ppm, from 1500 ppm to 2000 ppm, or from 500 ppm to 500 ppm).

Also disclosed herein are beverages and food products including the compositions disclosed herein. Also disclosed herein is milk including the compositions disclosed herein.

Also disclosed herein are methods for treating or preventing a microbial infection in a subject. As used herein, by a "subject" is meant an individual. The "subject" can include a mammal, such as a primate or a human. In some embodiments, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds.

In some embodiments, the amount of the first essential oil, second essential oil, and optional additional essential oils is sufficiently low to provide a composition that is non-toxic to the subject, particularly when used in a beverage or food product, but also in other products such as shampoos, lotions, and the like.

The methods for treating or preventing a microbial infection in a subject can comprise administering to the subject an effective amount of any of the compositions disclosed herein. The compositions described herein can be useful for treating microbial infections in humans (e.g., pediatric and geriatric populations) and in animals (e.g., veterinary applications). Microbial infections include, for example, bacterial, viral, and fungal infections. Bacterial infections include infections caused by bacilli, cocci, spirochaetes, and vibrio bacteria. In some examples, the microbial infection is a bacterial infection (e.g., a Gram positive bacterial infection). In some examples, the bacterial infection is a *Staphylococcus* infection, such as a *Staphylococcus aureus*. The compositions described herein are useful in treating a variety of *Staphylococcus aureus* infections, including drug-resistant *Staphylococcus aureus* infections and biofilm-associated *Staphylococcus aureus* infections. In some embodiments, the *Staphylococcus aureus* infection is methocillin-resistant *S. aureus* (MRSA). For example, the MRSA can be hospital-associated MRSA or community associated MRSA. In some examples, the bacterial infection is an *Escherichia* infection, such as *Escherichia coli* (*E. coli*). The compositions described herein are useful in treating a variety of *E. coli* infections.

Also disclosed herein are methods for combating bovine mastitis, the methods comprising applying any of the compositions disclosed herein to cow udders. Bovine mastitis is an inflammatory reaction of the udder tissue. In some examples, mastitis can be a potentially fatal mammary gland infection. Mastitis usually occurs when white blood cells (e.g., leukocytes) are released into the mammary gland, usually in response to bacteria invading the teat canal. The milk-secreting tissue and various ducts throughout the mammary gland can be damaged due to toxins released by the bacteria. Bacteria that can cause mastitis include, but are not limited to, *Pseudomonas aeruginosa, Staphylococcus aureus, Staphylococcus epidermidis, Streptococcus agalactiae, Streptococcus uberis, Brucella melitensis, Corynebacterium bovis, Mycoplasma* spp., *Escherichia coli* (*E. coli*), *Klebsiella pneumoniae, Klebsiella oxytoca, Enterobacter aerogenes, Pasteurella* spp., *Trueperella pyogenes*, and *Proteus* spp.

The methods of treatment or prevention described herein can further include treatment with one or more additional agents (e.g., an antimicrobial agent such as an antibacterial agent, an antifungal agent and/or an antiviral agent). The one or more additional agents and the compositions described herein can be administered in any order, including simultaneous administration, as well as temporally spaced order of up to several days apart. The methods can also include more than a single administration of the one or more additional agents and/or the compositions described herein. The administration of the one or more additional agents and the compositions described herein can be by the same or different routes. When treating with one or more additional agents, the compositions described herein can be combined into a pharmaceutical formulation that includes the one or more additional agents.

The methods and compositions as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compositions described herein are administered to a subject prior to onset (e.g., before obvious signs of a microbial infection), during early onset (e.g., upon initial signs and symptoms of a microbial infection), or after an established inflammatory response or development of a microbial infection. Prophylactic administration can occur for several days to years prior to the manifestation of symptoms of an infection. Prophylactic administration can be used, for example, in the preventative treatment of subjects exposed to *Staphylococcus aureus*. Therapeutic treatment involves administering to a subject a therapeutically effective amount of the compositions described herein after a microbial infection is diagnosed.

Herein, it was determined that combinations of selected essential oils resulted in a solution/material which had no odor per se or which had a null effect, yet still possessed the desired antimicrobial activity. There are many applications where it is desired that the final product have no odor. The combining of two or more essential oils to obtain a formulation having antimicrobial properties which has no (or a neutral) odor extends the use of essential oils to such applications.

For example, these selected "no-odor"/"low-odor" combinations permit the use of safe and effective essential oils in biocontrol formulations (e.g., antimicrobial formulations) for use in beverage and food products (e.g., milk, cheese, etc.) where the presence of any definable odor counter to the odor normally associated with the product/materials would be objectionable.

The non-odiferous essential oil based biocontrol/antimicrobial products that are, for example, effective against *E. coli* and/or *S. aureus* can be used to combat bovine mastitis. Such a product could be used as a cleanser or in conjunction with a cleanser, or as a cream to treat cow udders.

Furthermore, these essential oil compositions can be incorporated into formulations containing defined active ingredients such that the effectiveness of the final formulation is greater than when only the active ingredient is present. Additionally, other materials may be added to the formulation(s) which impart other characteristics (e.g., resist desiccation, improve retention of actives on hair etc.). For example, incorporation of the two or more essential oils or related compounds in a formulation which is ethanol-based (or that includes a similar volatile chemical) results in a product which quickly disinfects then evaporates to dryness leaving the surface/material dry and pristine. Incorporation of the two or more essential oils or related compounds in a formulation which is soap-based, for example, can result in a disinfectant soap which can disinfect while also removing debris, dirt, detritus, dead cells, etc., leaving a cleaned surface which has also been disinfected. Soaps/cleaners/cleansers can be created, for example, that contain fatty acids that retard the volatilization of the two or more essential oils (or related compounds), creating a soap/cleaner/cleanser which not only cleans and disinfects but has residual disinfection properties because of the retention of the two or more essential oils. In a specific application, the two or more essential oils or related chemicals may be formulated in a shampoo where the properties of the shampoo can facilitate the binding/adsorption of the shampoo on animal hair/fur. In a further embodiment, the two or more essential oils may be formulated with compounds that replenish/restore skin, hair, etc., such as a lotion or shampoo.

The above compositions have uses for humans, pets, livestock, etc. (e.g., animals with skin/hair). For humans, the uses include, but are not limited to: hand soaps, hand sanitizers, body soaps and lotions, skin lotions and creams, shampoos, conditioners, and rinses, facial products, cosmetics, lip balm and lipsticks, ophthalmic solutions (e.g., eye drops), and toothpastes.

The essential oils may be directly applied as a hard or liquid material, in lotions, creams, conditioners, moisturizers, either directly or through an applicator (e.g. for animals in a dip). The essential oils could be formulated with laundry products that use laundering conditions appropriate for the maintenance of the antimicrobial properties of the compositions. The above illustrations also have uses for the washing and disinfection of fruits and vegetables.

The above compositions are further illustrated below through a series of examples, where the examples include two or more essential oils optionally in combination with: a) other known microbials, b) other known surfactants, c) solvents/base formulations, etc. The selection of the components to be used in the examples was based upon showing efficacy/utility and the breadth of the chemistry under which the concept works.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process.

In the following examples, the essential oils used to prepare the formulations were concentrated solutions in ethanol. Control experiments were conducted to show that the ethanol was only a vehicle for the oils and did not contribute to antimicrobial activity. Antimicrobial effective formulations are those that resulted in a 5 log reduction in microbe population after 15 to 30 s exposure. In all timed experiments, the active ingredients were neutralized at pre-determined times to ensure that there was no residual activity present past the set-point. LUSTR-282® is an edible wax used to coat fruit. Typically such waxes may be added up to 20%. TOMAKOTE-8® (also an edible wax) can be used in place of LUSTR-282® or in combination with LUSTR-282®. Such formulations are advantageous for application such as teat-dips where good coverage and good residual activity are desired.

Example 1

Formulation A was prepared containing spearmint oil (0.1%) and thyme oil (0.1%) in combination with glycolic acid (3%), Witconate® surfactant (1.6%), and Natrosol® hydroxyethylcellulose (0.4%). Formulation A was prepared with a pH of 3.3. Formulation A reduced the *E. coli* challenge and the *S. aureus* challenge both by 5 log. Efficacy was established in aqueous solution and in aqueous solution with milk added as an interfering substance. In the aqueous solution with milk added, no odor change was detected.

Example 1a

Formulation A2 was prepared in the same manner as Formulation A above, but with the spearmint oil and thyme oil both at 0.05%. Formulation A2 reduced the *E. coli* challenge and the *S. aureus* challenge both by 4 log. Efficacy was established in aqueous solution and in aqueous solution with milk added as an interfering substance. In the aqueous solution with milk added, no odor change was detected.

Example 1b

Formulation A3 was prepared as above for either Formulation A or A2, but with PHMB added at 500 ppm. Formulation A3 reduced the *E. coli* challenge and the *S. aureus* challenge both by 4 log. Efficacy was established in aqueous solution and in aqueous solution with milk added as an interfering substance. In the aqueous solution with milk added, no odor change was detected.

Example 2

Formulation B was prepared as Formulation of A above, to which was added a wax carrier, LUSTR-282® (5%). Formulation B reduced the *E. coli* challenge and the *S. aureus* challenge both by 5 log. Efficacy was established in aqueous solution and in aqueous solution with milk added as an interfering substance. In the aqueous solution with milk added, no odor change was detected.

Example 3

Formulation C was prepared as Formulation of B above, to which was added a wax carrier, TOMAKOTE 8® (5%). Formulation C reduced the *E. coli* challenge and the *S. aureus* challenge both by 5 log. Efficacy was established in aqueous solution and in aqueous solution with milk added as an interfering substance. In the aqueous solution with milk added, no odor change was detected.

Example 4

Formulation D was prepared as Formulation B above, to which was added wax carriers, TAMAKOTE 8® (0 to 5%) or LUSTR-282 (0 to 5%). Formulation D reduced the *E. coli* challenge and the *S. aureus* challenge both by 5 log. Efficacy was established in aqueous solution and in aqueous solution with milk added as an interfering substance. In the aqueous solution with milk added, no odor change was detected.

Example 5

Formulation E was prepared containing sandalwood oil (0.05% to 0.1%), thyme oil (0.05 to 0.1%), and spearmint oil (0.05 to 0.1%). No odor was detected for the ternary Formulation E.

Example 6

The binary combination of spearmint oil (0.1%) and pine oil (0.1%) resulted in 5 log reduction of the microbial populations, but possessed a strong odor.

Example 7

The following formulations were antimicrobial effective, but possessed odor:
1) Orange oil (0.1%) and 500 ppm of PHMB;
2) Thyme Oil (0.1%) and 500 ppm of PHMB;
3) Spearmint Oil (0.1%) and 500 ppm of PHMB;
4) Dill Oil (0.1%) and 500 ppm of PHMB;
5) Sandalwood Oil (0.1%) and 500 ppm of PHMB;
6) Thyme Oil (0.1%), Pine Oil (0.1%) 500 ppm of PHMB.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:
1. An antimicrobial composition comprising:
a first essential oil; and
a second essential oil, wherein the first essential oil is spearmint oil and the second essential oil is thyme oil, wherein the first essential oil and the second essential oil are each present in concentrations of 0.05% to 0.1% by weight, and wherein the composition is substantially odorless.

2. The composition of claim 1, wherein the composition further comprises a third essential oil.

3. The composition of claim 2, wherein the third essential oil is present in a concentration of 0.05% to 0.2% by weight.

4. The composition of claim 2, wherein the third essential oil is sandalwood oil.

5. The composition of claim 1, wherein the composition further comprises a solvent.

6. The composition of claim 1, wherein the composition further comprises polyhexamethylene biguanide.

7. The composition of claim 6, wherein the polyhexamethylene biguanide is present in an amount of 100 to 2000 ppm.

8. The composition of claim 1, wherein the composition additionally comprises a wax carrier.

9. The composition of claim 1, wherein the composition has a pH of 7.5 or less.

10. The composition of claim 1, wherein the composition results in at least 5 log reduction in a population of microbes.

11. The composition of claim 10, wherein the microbes are one or more microorganisms selected from the group consisting of *Staphylococcus aureus* and *Escherichia coli*.

12. The composition of claim 1, wherein the composition is a soap, a cleanser, a hand sanitizer, a shampoo, a dip, a splash, a lotion, a cosmetic, a toothpaste, an ophthalmic solution, or a laundry product.

13. A beverage or food product, including the composition of claim 1.

14. Milk including the composition of claim 1.

15. A method for combating bovine mastitis in a cow suffering from bovine mastitis, comprising applying a therapeutically effective amount of the composition of claim 1 to the cow's udder.

16. A method for treating a microbial infection in a subject in need thereof, comprising administering to the subject a therapeutically effective amount of the composition of claim 1.

* * * * *